United States Patent [19]

Gutierrez et al.

[11] Patent Number: 5,472,642

[45] Date of Patent: Dec. 5, 1995

[54] DIAMINOALKYL DI(SULFOSUCCINATES) AND THEIR USE AS BUILDERS

[75] Inventors: Eddie N. Gutierrez, Midland Park; Shang-Ren Wu, Mahwah, both of N.J.

[73] Assignee: Lever Brothers Company, Division of Conopco Inc., New York, N.Y.

[21] Appl. No.: 362,358

[22] Filed: Dec. 22, 1994

[51] Int. Cl.$^6$ ............................ C11D 3/33; C11D 3/34; C11D 1/04; C11D 1/18

[52] U.S. Cl. ................ 252/545; 252/546; 252/174.19; 562/102; 562/106

[58] Field of Search ............................ 562/102, 106; 252/545, 546, 174.19

[56] References Cited

U.S. PATENT DOCUMENTS

| | | | |
|---|---|---|---|
| 3,128,287 | 4/1964 | Berg | 542/252 |
| 3,151,084 | 9/1964 | Schlitz et al. | 252/137 |
| 3,692,685 | 9/1972 | Lamberti et al. | 252/89 |
| 3,920,564 | 11/1975 | Grecsek | 252/8.6 |
| 3,925,375 | 12/1975 | Lamberti | 544/110 |
| 3,957,775 | 5/1976 | Lamberti | 544/110 |
| 4,397,776 | 8/1983 | Ward | 252/527 |
| 4,560,491 | 12/1985 | Sherman | 252/106 |
| 4,663,071 | 5/1987 | Bush et al. | 252/174.19 |
| 4,701,284 | 10/1987 | Hendricks et al. | 562/106 |
| 4,704,233 | 11/1987 | Hartman et al. | 252/527 |
| 5,068,420 | 11/1991 | Kreczmer | 562/583 |
| 5,104,568 | 4/1992 | Shaw, Jr. et al. | 252/174.18 |
| 5,254,281 | 10/1993 | Pichardo et al. | 252/108 |
| 5,258,141 | 11/1993 | Crump et al. | 252/546 |
| 5,296,588 | 3/1994 | Au et al. | 536/1.11 |
| 5,336,765 | 8/1994 | Au et al. | 536/18.5 |

OTHER PUBLICATIONS

Defensive Publication No. T. 101,805 May 4, 1992.

*Primary Examiner*—Paul Lieberman
*Assistant Examiner*—E. Harriman
*Attorney, Agent, or Firm*—James J. Farrell

[57] ABSTRACT

Diaminoalkyl di(sulfosuccinate) compounds useful as builders are disclosed together with a method for their preparation and detergent compositions for their use.

7 Claims, No Drawings

DIAMINOALKYL DI(SULFOSUCCINATES) AND THEIR USE AS BUILDERS

BACKGROUND OF THE INVENTION

1. Field of the Invention

The invention relates to diaminoalkyl di(sulfosuccinates) (DDSS) compounds and their use as builders.

2. Related Art

The use of aminopolycarboxylates as laundry detergent additives is generally disclosed in the art. For example, the prior art described laundry detergent compositions which include nitrilotriacetates (NTA), ethylendediaminetetraacetates (EDTA), diethylenetriaminepentaacetates (DTPA), and hydroxyethylethylenediaminetriaacetates (HEDTA), and triethylenetetramine hexaacetic acid (TTHA).

U.S. Pat. No. 4,560,491 discloses laundry detergent compositions containing an aluminasilicate or organic detergency builder and from about 0.5% to about 10% by weight of HEDTA. The list of suitable organic detergency builders disclosed includes aminopolycarboxylates such as NTA, EDTA and DTPA.

U.S. Pat. No. 4,397,776 discloses liquid laundry detergent compositions having a pH between 9 and 13, containing alpha-amine oxide surfactants and from about 0.01% to about 25% by weight of a heavy-metal chelating agent. The preferred chelating agents include aminopolycarboxylates such as NTA, EDTA, DTPA and HEDTA.

U.S. Pat. No. 3,920,564 discloses softener/detergent formulations containing surfactants, quaternary ammonium or diamine fabric softeners, and a builder salt selected from aminopolycarboxylates and/or sodium citrate. Examples of suitable aminopolycarboxylates include NTA, EDTA and HEDTA.

U.S. Pat. No. 3,151,084 discloses alkylbenzenesulfonate-containing detergent compositions in which solubility is said to be improved by the addition of a mixture of EDTA and a solubilizing agent selected from salts of N,N-di(2-hydroxyethyl) glycine, iminodiacetic acid, NTA and HEDTA.

U.S. Pat. No. 4,704,233 discloses detergent compositions containing ethylenediamine N-N'disuccinic acid and salts.

None of these patents or applications disclose either DDSS and its salts or detergent compositions containing it. Moreover, the aminopolycarboxylates disclosed in those patents or applications are not biodegradable.

The art also discloses methods of synthesizing mono aminoalkyl sulfosuccinates and mono iminoalkyl sulfosuccinates in Lamberti, U.S. Pat. No. 3,957,775.

None of these references disclose the DDSS or compositions of the present invention or recognize the unique builder properties of DDSS in the context of laundry detergent compositions.

SUMMARY OF THE INVENTION

The compounds of this invention are generally of the formula:

$$\begin{array}{c} SO_3^-M^+ \quad H \quad \diagdown_N \diagup CH_2-R_1-CH \diagup^{R_2} \diagdown_N \diagup H \quad SO_3^-M^+ \\ | \qquad \qquad | \qquad \qquad \qquad \qquad \qquad \qquad | \qquad \qquad | \\ COO^-M^+ \quad COO^-M^+ \qquad \qquad \qquad \qquad COO^-M^+ \quad COO^-M^+ \end{array}$$

where M is alkali or alkaline earth metal but preferably sodium; and where $R_1$ is optionally present and when present is CHOH or $CH_2$ and $R_2$ is H. When $R_1$ is not present the chain is simply an ethylene diamine group connecting the two sulfosuccinates and $R_2$ is methyl or hydrogen.

The compositions of this invention are laundry detergents comprising (a) from about 1% to about 75% by weight of a detergent surfactant selected from the group consisting of anionic surfactants, nonionic surfactants, switterionic surfactants, ampholytic surfactants, cationic surfactants, and mixtures thereof; (b) from about 5% to about 80% by weight of a primary detergency builder; and (c) from about 0.1% to about 75% by weight of DDSS alkali metal, alkaline earth metal, ammonium or substituted ammonium salts thereof, or mixtures thereof as a secondary builder. The DDSS can, if desired, be used as the sole builder.

It is thus seen as desirable to produce DDSS in good yield for use as a builder salt.

A workable and cost-efficient production of DDSS and its salts must be directed towards optimizing the process conditions in such a manner that reasonable yields are obtained.

Accordingly, it is an object of the present invention to provide DDSS and its salts and detergent compositions employing DDSS as a builder.

This and other objects and advantages will appear as the description proceeds.

The attainment of the above objects is made possible by this invention which includes DDSS compounds and compositions containing them.

The DDSS may be prepared by the following process: reaction of sulfur trioxide with maleic anhydride at a mole ratio of the sulfur trioxide to maleic anhydride of about 1.1:1 to 1.3:1 and a temperature of 60° C. to 80° C. to form the sulfo maleic anhydride.

Addition of water and ice to the sulfo maleate and reduction of the pH to about 1 at a temperature of 25° C. to 30° C. in the absence of alkali or alkaline earth metal to retain the double bond and to form the sulfo maleic acid.

Addition of the diaminoalkyl moiety to the sulfo maleic acid together with the alkali or alkaline earth metal hydroxides or mixtures of these hydroxides to about pH 11. The temperature is maintained at about 25° C. to 50° C. and preferably 25° C. to 35° C. with agitation for about 2 to 5 hours. The diaminoalkyl moiety may be ethylenediamine, 1,3 propylene diamine, 2, hydroxy-1,3 propylene diamine and 1,2 propylenediamine.

After formation, the material is suitably recovered by vacuum distillation. The process produces a good yield of DDSS.

The DDSS as mentioned above has the formula:

$$\begin{array}{c} SO_3^-M^+ \quad H \quad \diagdown_N \diagup CH_2-R_1-CH \diagup^{R_2} \diagdown_N \diagup H \quad SO_3^-M^+ \\ | \qquad \qquad | \qquad \qquad \qquad \qquad \qquad \qquad | \qquad \qquad | \\ COO^-M^+ \quad COO^-M^+ \qquad \qquad \qquad \qquad COO^-M^+ \quad COO^-M^+ \end{array}$$

where M is alkali or alkaline earth metal but preferably sodium; and wherein $R_1$ is optionally present and when present is CHOH or $CH_2$ and $R_2$ is H. When $R_1$ is not present the chain is simply an ethylene diamine group connecting the two sulfosuccinates and $R_2$ is methyl or hydrogen.

Preferably $R_1$ is not present and $R_2$ is hydrogen so that the two sulfosuccinate groups are connected by ethylenediamine. The compounds which may be included are alkali metal or alkaline earth metal salts of ethylene diamine di(sulfosuccinate), 1,3 propylene diamine di(sulfosuccinate) 1,2 propylene diamine di(sulfosuccinate), and 2, hydroxy 1,3 propylene diamine di(sulfosuccinate).

DESCRIPTION OF THE PREFERRED EMBODIMENT

Synthesis of Sulfosuccinates

Sulfur trioxide reacts with maleic anhydride to afford sulfo maleic anhydride (SMA) according to the following reaction scheme:

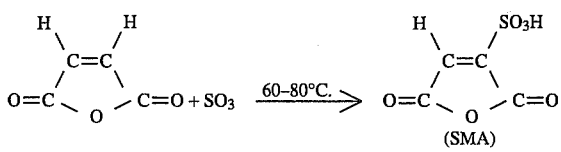

Because of the presence of the sulfonic acid group, sulfomaleic anhydride (SMA) is a much more reactive electrophile than maleic anhydride and will therefore react rapidly with nucleophiles under aqueous Michael conditions.

Diamine derivatives add to either the sodium or calcium salts of SMA. When the starting Michael addend is a diamine, such as alkyldiamine for example, ethylene diamine, then diaddition to sulfomaleate occurs as the following reaction scheme shows to produce ethylene diamine di(sulfosuccinate).

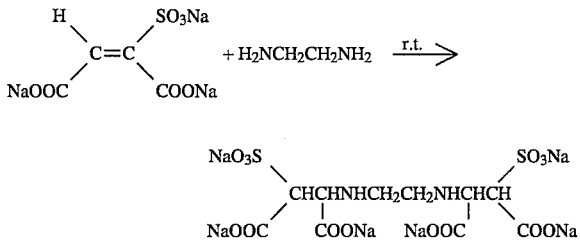

Ethylenediamine di(sulfosuccinate) (EDDSS) has eight ligands for binding which make this material a good builder. Sodium sulfo azadisuccinate (SADS), on the other hand, has six ligands.

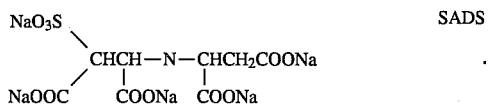

Amino based sulfo succinates are produced by reacting either an amine or amine carboxylate(s) with the sulfo maleate at pHs of about 9–12 and at a temperature of about 25° C. Either calcium or sodium salts or mixtures of both can be employed, however, it is more convenient to use sodium because the amine builders appear to strongly complex calcium, and pose a removal problem. The addition, unlike the hydroxy acid route, produces a mixture of RS,SR, RR,SS isomers.

Calcium Binding

The log $K_{ca}$ of RS,SR hexasodium ethylenediamine di(sulfosuccinate) was calculated to be 8 with an SC5 of 1.6.

In general, the process involves running the reaction at a sufficient temperature for a sufficient time to form the final product while maintaining the following parameters:

The alkali or alkaline earth metal hydroxide or mixtures employed in the reaction mixtures of the inventive process is selected from the group consisting of sodium, potassium, lithium or barium hydroxide, or strontium hydroxide, or magnesium, or calcium hydroxide or mixtures of these. The most preferred alkali metal hydroxide for use in this invention is sodium hydroxide.

The DDSS salt forming reaction of the present invention is conducted at high concentration in aqueous media to afford efficacy and high throughput. The amount of water present may vary and is preferably sufficient to permit the reaction to proceed with the amount of water being about 55% to 95%. The amount may, however, be more or less depending on design parameters.

Desirably, the reactants of the starting mixture for the process are combined in water using physical agitation. In the preferred embodiments of the invention, the alkali or alkaline earth metal hydroxide or mixture is mixed with an aqueous mixture of the alkyldiamine and sulfo maleate moieties with agitation. The reaction is conducted at atmospheric pressure.

The reaction temperature for the process is preferably at room temperature, 25° C. or cooler. The reaction temperature is maintained for at least about 2 hours and preferably no longer than about 5 hours at temperatures ranging from 20° C. to 35° C. The aqueous reaction product typically contains a mixture of DDSS, alkyldiamine and sulfomalate.

The reaction products obtained by the processes of this invention contain the alkali or alkaline earth metal or mixture of salts of DDSS and may be worked up by methods known in the art.

At any stage after the DDSS salt formation, the reaction product can be concentrated by removal of water to the desired extent. Water removal can, for example, involve substantially complete drying of the reaction product mixture, e.g., by spray drying, so that the DDSS salt is recovered in solid, e.g., granular form. The sodium salt of DDSS in the form of aqueous liquid may be utilized directly in the preparation of detergent compositions or laundry additive products of the types more fully described hereinafter.

When converted into suitable form, the DDSS salts can be used as sequestering builders in a wide variety of detergent or laundry additive compositions.

Detergent compositions incorporating the DDSS salt prepared using the processes of this invention contain as essential components from about 0.5% to about 98% of a surfactant and from about 0.1% to about 75% of the DDSS compounds as a detergency builder or secondary detergency builder, generally in sodium-salt form. Surfactants that are useful in the present invention are the anionic (soap and nonsoap), nonionic zwitterionic and ampholytic compounds. The chemical nature of these detergent compounds is not an essential feature of the present invention. Moreover, such detergent compounds are well known to those skilled in the detergent art and the patent and printed literature are replete with disclosures of such compounds. Typical of such literature are "Surface Active Agents" by Schwartz and Perry and Berch, the disclosures of which are incorporated by reference herein. The DDSS builder can be used either as the sole builder or where desired can be used in conjunction with other well-known builders, examples of which include water-soluble salts of phosphates, pyrophosphates, orthophosphates, polyphosphates, phosphonates, carbonates, polyhydroxy-sulfonates, polyacetates, carboxylates, polycarboxylates, succinates and the like.

In addition to the surfactant and builder, there may be optionally present additional ingredients which enhance the performance of the detergent composition. Typical examples thereof include the well known soil suspending agents, hydrotropes, corrosion inhibitors, dyes, perfumes fillers, optical brighteners, enzymes, suds boosters, suds depressants, germicides, anti-tarnishing agents, cationic detergents, softeners, bleaches, buffers and the like.

The detergent compositions of the present invention may be in any of the usual physical forms for such compositions, such as powders, beads, flakes, bars, tablets, noodles, liquids, pastes and the like. The detergent compositions are prepared and utilized in the conventional manner. The wash solutions thereof desirably have a pH from about 7 to about 12, preferably from about 9 to about 11.

In addition to their utility as builders in detergent and laundry additive compositions, the DDSS salts of the invention can also be utilized in other contexts wherein water hardness sequestration is required. Other uses are provided in water softening compositions, devices and methods and boiler descaling compositions and methods. It is also theorized that DDSS can complex heavy metals which react with bleach and thus can stabilize bleach.

It should also be noted that DDSS has utility in metal cleaning compositions under pH conditions of about 2 to about 5.

The following examples are designed to illustrate, but not to limit, the practice of the instant invention. All percentages and parts herein are by weight unless indicated otherwise. All ratios herein are mole ratios unless indicated otherwise.

The NMR is a 200 MHz Bruker model. Samples are prepared by dissolution in $D_2O$.

EXAMPLE 1

0.1 mole of sulfomaleic anhydride is dissolved in about 50 ml of water and stirred. 0.3 mole of sodium bicarbonate is then added to a pH of about 9 and the solution is cooled to maintain it at about 25° C. (room temperature). 0.05 mole of ethylenediamine is added with continued agitation and the pH is maintained at 11 by addition of sodium hydroxide if necessary. The temperature is still maintained at 25° C. After five hours of reaction time, the solution is evaporated to dryness on a rotoval and dried in an oven. The material obtained is hexasodium ethylenediamine di(sulfosuccinate).

| $^1$H NMR | | |
| --- | --- | --- |
| C$H_2$N | multiplet | 2.5–2.7δ |
| CHN | multiplet | 3.4–3.6δ |
| CHSO$_3$ | multiplet | 3.75–3.84δ |
| C$^{13}$ NMR | | |
| CH$_2$N | 4 singlets | 51–53 ppm |
| CHN | 4 singlets | 67–69 ppm |
| CHSO$_3$ | 3 singlets | 74–76 ppm |
| COONa | 4 singlets | 176–184 ppm |

EXAMPLE 2

0.1 mole of sulfomaleic anhydride is dissolved in about 50 ml of water and stirred. 0.3 mole of sodium bicarbonate is then added to a pH of about 9 and the solution is cooled to maintain it at about 25° C. (room temperature). 0.05 mole of 2 hydroxy 1,3 propylenediamine is added with continued agitation and the pH is maintained at 11 by addition of sodium hydroxide if necessary. The temperature is still maintained at 25° C. After five hours of reaction time, the solution is evaporated to dryness on a rotoval and dried in an oven. The material obtained is hexasodium 2 hydroxy 1,3 propylenediamine di(sulfosuccinate).

| $^1$H NMR | | |
| --- | --- | --- |
| CH$_2$N | multiplet | 2.2–2.6δ |
| CHN | multiplet | 3.4–3.6δ |
| CHOH | multiplet | 3.4–3.6δ |
| CHSO$_3$ | multiplet | 3.75–3.84δ |
| C$^{13}$ NMR | | |
| CH$_2$N | 4 singlets | 55.5–57 ppm |
| CHN | 4 singlets | 68–70 ppm |
| CHOH | 4 singlets | 72.5–75 ppm |
| CHSO$_3$ | 4 singlets | 75.5–76 ppm |
| COONa | 5 singlets | 176–184 ppm |

EXAMPLE 3

0.1 mole of sulfomaleic anhydride is dissolved in about 50 ml of water and stirred. 0.3 mole of sodium bicarbonate is then added to a pH of about 9 and the solution is cooled to maintain it at about 25° C. (room temperature). 0.05 mole of 1,3 propylenediamine is added with continued agitation and the pH is maintained at 11 by addition of sodium hydroxide if necessary. The temperature is still maintained at 25° C. After five hours of reaction time, the solution is evaporated to dryness on a rotoval and dried in an oven. The material obtained is hexasodium 1,3 propylenediamine di(sulfosuccinate).

| $^1$H NMR | | |
| --- | --- | --- |
| CH$_2$ | multiplet | 1.3–1.7δ |
| CH$_2$N | multiplet | 2.4–2.8δ |
| CHN | doublet of doublets | 3.4–3.6δ |
| CHSO$_3$ | doublet of doublets | 3.6–3.8δ |
| C$^{13}$ NMR | | |
| CH$_2$ | 4 singlets | 37.5–39 ppm |
| CH$_2$N | 2 singlets | 50 ppm |
| CHN | 2 singlets | 68–70 ppm |
| CHSO$_3$ | 2 singlets | 75–76 ppm |
| COONa | 5 singlets | 173–184 ppm |

EXAMPLE 4

An aqueous crutcher slurry containing 46% by weight of water is spray-dried in a counter-current spray-drying tower to a base powder having a bulk density of 710 g/liter and a moisture content of 15.8%. The formulation of the powder prepared is as follows:

| | Parts by Weight |
| --- | --- |
| $C_{12}$–$C_{15}$ alcohol 7EO ethoxylate | 3.0 |
| DDSS | 23.0 |
| Sodium carbonate | 5.0 |
| Sodium silicate | 6.0 |
| Water and minor components | 10.0 |

A mixture of anionic and nonionic surfactants containing 3.8 parts of $C_{10-13}$ alkylbenzene sulfonic acid and parts of a $C_{12-15}$ primary alcohol 7EO ethoxylate prepared by neutralizing the sulfonic acid with caustic soda solution of 50% by weight is prepared. This mixture is then heated under vacuum until the water content is reduced to about 3%, resulting in a mole ratio of water to anionic of 1.6. This mixture is then sprayed onto the powder.

A liquid mixture of sodium monostearyl phosphate and petroleum jelly in a weight ratio of 1.3:1 is then sprayed onto the powder at the rate of 0.8 parts to 63 parts.

Finally, the powder is dosed with heat-sensitive components such as oxygen bleaches, perfumes and enzymes in accordance with conventional practice to produce a finished powder having the following composition:

|  | Parts by Weight |
|---|---|
| Sodium C$_{10-13}$ alkylbenzene sulfonate | 4.0 |
| C$_{12}$–15 primary alcohol ethoxylate 7EO | 9.0 |
| hexasodium ethylenediamine di(sulfosuccinate) | 23.0 |
| Sodium carbonate | 5.0 |
| Sodium silicate | 6.0 |
| Sodium sulfate | 26.9 |
| Sodium perborate | 12.0 |
| Sodium carboxymethylcellulose | 0.9 |
| Sodium stearyl phosphate | 0.2 |
| Petroleum jelly | 0.6 |
| Enzyme marumes | 0.4 |
| Cellulose ether anti-redeposition aid | 0.3 |
| Water, perfume, and minor components to | 100.0 |

The finished powder produced will have a bulk density of about 800 g/liter.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. Diaminoalkyl di(sulfosuccinate) compounds of the formula:

$$SO_3^-M^+ \quad H \diagdown_N \diagup^{CH_2-R_1-CH} \diagdown_N \diagup^{H} \quad SO_3^-M^+$$
$$COO^-M^+ \quad COO^-M^+ \qquad\qquad COO^-M^+ \quad COO^-M^+$$

with $R_2$ on the central N, wherein M is alkali or alkaline earth metal or a mixture; and R$_1$ is either present or absent and when present is CH$_2$ or CHOH and R$_2$ is H, when R$_1$ is not present R$_2$ is methyl or hydrogen.

2. A compound as defined in claim 1 wherein R$_1$ is absent and M is sodium.

3. A compound as defined in claim 1 wherein R$_1$ is absent, R$_2$ is methyl and M is sodium.

4. A compound as defined in claim 1 wherein R$_1$ is CH$_2$ and M is sodium.

5. A compound as defined in claim 1 wherein R$_1$ is CHOH and M is sodium.

6. A method for chelating alkaline earth metal ions comprising contacting said ions with a diaminoalkyl di(sulfosuccinate) of the formula:

$$SO_3^-M^+ \quad H \diagdown_N \diagup^{CH_2-R_1-CH} \diagdown_N \diagup^{H} \quad SO_3^-M^+$$
$$COO^-M^+ \quad COO^-M^+ \qquad\qquad COO^-M^+ \quad COO^-M^+$$

wherein M is alkali or alkaline earth metal or a mixture; and

R$_1$ is either present or absent and when present is CH$_2$ or CHOH and R$_2$ is H, when R$_1$ is not present R$_2$ is methyl or hydrogen.

7. A detergent composition comprising 2–98% of an anionic, nonionic, zwitterionic or cationic surfactant and 0.1 to 75% of a diaminoalkyl di(sulfosuccinate) of the formula:

$$SO_3^-M^+ \quad H \diagdown_N \diagup^{CH_2-R_1-CH} \diagdown_N \diagup^{H} \quad SO_3^-M^+$$
$$COO^-M^+ \quad COO^-M^+ \qquad\qquad COO^-M^+ \quad COO^-M^+$$

wherein M is alkali or alkaline earth metal or a mixture; and

R$_1$ is either present or absent and when present is CH$_2$ or CHOH and R$_2$ is H, when R$_1$ is not present R$_2$ is methyl or hydrogen.

* * * * *